United States Patent
Garault et al.

(10) Patent No.: US 11,166,473 B2
(45) Date of Patent: Nov. 9, 2021

(54) LACTOBACILLUS RHAMNOSUS FOR USE IN PREPARATION OF FERMENTED PRODUCTS

(71) Applicant: COMPAGNIE GERVAIS DANONE, Paris (FR)

(72) Inventors: Peggy Garault, Montlhery (FR); Daval Christophe, Choisy le Roi (FR); Laurent Marchel, Villemoisson sur Orge (FR)

(73) Assignee: COMPAGNIE GERVAIS DANONE, Paris (FR)

( * ) Notice: Subject to any disclaimer, the term of this patent is extended or adjusted under 35 U.S.C. 154(b) by 178 days.

(21) Appl. No.: 16/158,165

(22) PCT Filed: Apr. 14, 2016

(86) PCT No.: PCT/EP2016/058267
§ 371 (c)(1),
(2) Date: Oct. 11, 2018

(87) PCT Pub. No.: WO2017/178053
PCT Pub. Date: Oct. 19, 2017

(65) Prior Publication Data
US 2019/0082706 A1 Mar. 21, 2019

(30) Foreign Application Priority Data
Apr. 24, 2012 (CH) ................. CH00555/12

(51) Int. Cl.
A23C 9/123 (2006.01)
C12R 1/225 (2006.01)
A23C 11/10 (2021.01)

(52) U.S. Cl.
CPC .......... *A23C 9/1234* (2013.01); *A23C 9/1232* (2013.01); *A23C 11/106* (2013.01); *C12R 1/225* (2013.01); *A23Y 2220/15* (2013.01); *A23Y 2220/73* (2013.01); *A23Y 2240/75* (2013.01)

(58) Field of Classification Search
CPC .................................................... A23C 9/1234
See application file for complete search history.

(56) References Cited

U.S. PATENT DOCUMENTS

2003/0091694 A1* 5/2003 Remo ..................... A23L 11/09
426/52

FOREIGN PATENT DOCUMENTS

WO WO-2012136833 A1 * 10/2012 ............. C12R 1/225
WO WO 2012/136833 A1 10/2014

OTHER PUBLICATIONS

Muhammed Ramzan et al.: Evaluation of volatile flavouring compounds in Cheddar cheese, manufactured by using Lactobacillus rhamnosus as an adjunct culture, Journal of Agroalimentary Processes and Technologies 2010, 16 (2), pp. 188-195.

(Continued)

Primary Examiner — Stephanie A Cox
(74) Attorney, Agent, or Firm — Arent Fox LLP

(57) ABSTRACT

The present invention relates to a novel strain of *Lactobacillus rhamnosus*, compositions comprising said strain and to methods for the preparation of such compositions.

18 Claims, 5 Drawing Sheets

(56) References Cited

OTHER PUBLICATIONS

Champagne C P., et al, "Freeh-cheesemilk formulation fermented by a combination of freeze-dried citrate-positive cultures and exopolysaccharide-producing lactobacilli with liquid lactococcal starters," Food Research International Elsevier Applied Science, Barking, GB, vol. 39, No. 6, Jul. 1, 2006, pp. 651-659.

International Search Report dated Aug. 4, 2016 for PCT/EP2016/058267.

* cited by examiner

LACTOBACILLUS RHAMNOSUS FOR USE IN PREPARATION OF FERMENTED PRODUCTS

CROSS-REFERENCE TO RELATED APPLICATIONS

This application is a 35 U.S.C. 371 National Phase of International Patent Application No. PCT/EP2016/058267, filed on Apr. 14, 2016.

FIELD OF THE INVENTION

The present invention relates to a novel strain of *Lactobacillus rhamnosus*, compositions comprising said strain and to methods for the preparation of such compositions.

TECHNICAL BACKGROUND

Diacetyl (butanedione or butane-2,3-dione) and acetoin (3-hydroxybutanone or acetyl methyl carbinol) are commonly used food flavouring compounds that provide the characteristic flavor of butter and are often added to butter substitutes such as margarine to provide buttery flavours.

Diacetyl is produced industrially by dehydrogenation of 2,3-butanediol. However both diacetyl and acetoin are also by-products of lactic fermentation by certain strains of bacteria and various other micro-organisms. Heterolactic acid bacteria are able to produce diacetyl and acetoin as by-products alongside lactic acid. The use of *Lactobacillus rhamnosus* to provide flavor compounds such as diacetyl and acetoin is known in the art (WO 2012136832). *Lactobacillus rhamnosus* produce acetaldehyde from pyruvate and thiamine pyrophosphate, which condenses with pyruvate to provide alpha-acetolactate which is converted to diacetyl, which may also be further reduced to acetoin by diacetyl reductase. Acetoin is also formed by decarboxylation of alpha-acetolactate. However the quantity of diacetyl and acetoin formed is dependent the specific strain of *Lactobacillus rhamnosus* that is used (Medina de Figueroa Microbiol. Res. (2001) 155, 257-262). There exists a need for a cost-effective process of preparing food products with improved creamy and buttery organoleptic characteristics.

SUMMARY OF THE INVENTION

The present invention follows from the unexpected finding that a novel strain of *Lactobacillus rhamnosus* (hereinafter also referred to as *L. rhamnosus*) produces high amounts of diacetyl and acetoin which provides exceptional organoleptic characteristics to food products. Accordingly, the present invention provides a *Lactobacillus rhamnosus* strain deposited at the CNCM under reference number CNCM I-4993. The present invention also provides compositions comprising *L. rhamnosus* CNCM I-4993, and methods for the preparation thereof.

DETAILED DESCRIPTION OF THE INVENTION

As used herein the term "stable composition" shall be taken to mean a composition that does not present sedimentation and/or serum separation.

As used herein the term "x % (w/w)" is equivalent to "x g per 100 g". As used herein the terms "dairy composition", "milk-based composition" or "dairy product" shall be taken to mean a product or composition comprising essentially of or consisting of milk or milk components and optionally further ingredients.

As used herein the term "fermented dairy" shall be taken to mean a product or composition that is the product of the acidifying fermentation of a milk-based composition by a starter culture of fermenting microorganisms, in particular bacteria, preferably lactic acid bacteria. As used herein the term "fermented milk" shall be taken to mean a product or composition derived from milk by the acidifying action of at least one lactic acid bacterium. Accordingly, as used herein a fermented dairy product can thus be a fermented milk, such as a yoghurt (e.g. a set, stirred or drink yogurt), or a fresh cheese such as a white cheese or a "petit-Suisse". It can be also a strained fermented milk such as a strained yoghurt (e.g. a concentrated or Greek-style yoghurt).

The terms "fermented milk" and "yogurt" or "yoghurt" are given their usual meanings in the field of the dairy industry, that is, products suitable for human consumption and originating from acidifying lactic fermentation of a milk substrate. These products can contain secondary ingredients such as fruits, vegetables, sugar, etc. The expression "fermented milk" may be used to refer to fermented milks other than yogurts e.g. "Kefir", "Kumtss", "Lassi", "Dahi", "Leben", "Filmjolk", "Villi", "Acidophilus milk".

The term "yogurt" or "yoghurt" as used herein shall be taken to mean fermented milk obtained by the acidifying lactic fermentation of specific thermophilic lactic acid bacteria such as *Lactobacillus delbrueckii* subsp. *bulgaricus* and *Streptococcus thermophilus* (also referred to as *Streptococcus salivarius* subsp. *thermophilus*), which must be in the living state in the finished product at a minimum CFU. In certain countries, regulations allow the addition of further lactic acid bacteria to yoghurt such as but not limited to strains of *Bifidobacterium* and/or *Lactobacillus acidophilus* and/or *Lactobacillus casei*. These additional lactic acid bacteria strains are intended to impart various properties to the finished product, such as that of providing organoleptic qualities, favoring equilibrium of intestinal flora or modulating the immune system.

As used herein the term "strained fermented dairy composition" shall be taken to mean a fermented dairy composition which has been subjected to a post-fermentation acid whey separation process.

As used herein the term "spoonable" shall be taken to mean a solid or semi-solid that may be consumed by means of a spoon or other utensil.

As used herein the term "fermentation" shall be taken to mean the metabolism of a substance by microorganisms, e.g. bacteria, yeasts, or other microorganisms.

As used herein the term "cfu" or "CFU" shall be taken to be an abbreviation of the term "colony forming unit".

As used herein the term "CNCM I-" followed by a 4 digit number shall be taken to refer to a strain deposited at the Collection Nationale de Cultures de Microorganismes (CNCM) 25 rue du Docteur Roux, Paris, France under the Budapest Treaty with an accession number corresponding to said 4 digit number, e.g. CNCM I-4993.

As used herein reference to a bacterial strain or species shall be taken to include functionally equivalent bacteria derived therefrom such as but not limited to mutants, variants or genetically transformed bacteria. These mutants or genetically transformed strains can be strains wherein one or more endogenous gene(s) of the parent strain has (have) been mutated, for instance to modify some of their metabolic properties (e.g., their ability to ferment sugars, their resistance to acidity, their survival to transport in the gastrointestinal tract, their post-acidification properties or their metabolite production). They can also be strains resulting from the genetic transformation of the parent strain to add one or more gene(s) of interest, for instance in order to give to said genetically transformed strains additional physiological features, or to allow them to express proteins of therapeutic or prophylactic interest that one wishes to administer through said strains. These mutants or genetically transformed strains can be obtained from the parent strain by means of conventional techniques for random or site-directed mutagenesis and genetic transformation of bacteria, or by means of the technique known as "genome shuffling". In the present text, strains, mutants and variants derived from a parent species or strain will be considered as being encompassed by reference to said parent species or strain, e.g. the phrases "*Lactobacillus rhamnosus*" and "CNCM I-4993" shall be taken to include strains, mutants and variants derived therefrom.

Accordingly, as used herein reference to a bacterial strain specified by an accession or deposit number shall be taken to encompass variants thereof having at least 95% identity (see: Stackebrandt & Goebel, 1994, Int. J. Syst. Bacteriol. 44:846-849). In a particularly preferred embodiment, said variant has at least 97% identity with the 16S rRNA sequence of said specified strain, more preferably at least 98% identity, more preferably at least 99% or more identity.

As used herein the term "substantially pure" when used in reference to a bacterial strain refers to the percent of said bacterial strain relative to the total micro-organism content. Substantially pure can be at least about 99.99%, at least about 99.90%, at least about 99.50%, at least about 99.00%, at least about 95.00%, at least about 90.00%, at least about 85.00%, or at least about 75.00%.

As used herein, a "lactic acid bacterium" is a Gram-positive, acid-tolerant, generally non-sporulating and non-respiring, either rod- or cocci-shaped bacterium that is able to ferment sugars into lactic acid.

The present invention relates to a novel strain of *Lactobacillus rhamnosus*, compositions comprising said strain and to methods for the preparation of such compositions.

*Lactobacillus rhamnosus*

In a first aspect the present invention provides a strain of *Lactobacillus rhamnosus*. The *Lactobacillus rhamnosus* strain of the invention is characterized in that it is capable of secreting at least 150 parts per million (ppm) acetoin, preferably at least 200 parts per million (ppm) acetoin, further preferably at least 250 parts per million (ppm) acetoin. In one embodiment the *Lactobacillus rhamnosus* is characterized in that it is capable of secreting between 150 and 500 parts per million (ppm) acetoin. It is particularly preferred that the *Lactobacillus rhamnosus* strain of the invention is capable of secreting at least 20 parts per million (ppm) diacetyl, preferably at least 30 parts per million (ppm) diacetyl, further preferably at least 40 parts per million (ppm) diacetyl. In one embodiment the *Lactobacillus rhamnosus* is characterized in that it is capable of secreting between 20 and 100 parts per million (ppm) diacetyl. Methods for the measurement of diacetyl and acetoin secretion are known in the art, typically as provided herein the secretion thereof is measured by gas chromatography of supernatant after at least 16 hours culture in a milk-based medium. In a preferred embodiment the present invention provides a strain of *Lactobacillus rhamnosus* characterized in that it is capable of secreting at least 250 ppm acetoin and at least 20 ppm diacetyl.

The present invention provides the strain *Lactobacillus rhamnosus* CNCM I-4993. This strain has been isolated from nature and deposited at the Collection Nationale de Cultures de Microorganismes (CNCM) (Institut Pasteur, 25 Rue du Docteur Roux, Paris, France) under the Budapest Treaty on Jul. 1, 2015 under reference number CNCM I-4993. The deposit was made in accordance with the Budapest Treaty on the International Recognition of the Deposit of Microorganisms for the Purposes of Patent Procedure, as provided therein the applicant requests that a sample of the deposited micro-organisms only be made available to an independent expert, until the date on which the patent may be granted. In one embodiment the present invention provides the isolated strain *Lactobacillus rhamnosus* CNCM I-4993, preferably said isolate is substantially pure.

Compositions of the Invention

In a second aspect the present invention provides compositions comprising *Lactobacillus rhamnosus* CNCM I-4993. Preferably, the composition comprises at least $10^6$, more preferably at least $10^7$ and most preferably at least $10^8$ colony forming unit (CFU) *Lactobacillus rhamnosus* CNCM I-4993 per gram (g) of composition according to embodiments of the invention.

In embodiments, the composition comprises $10^5$ to $10^{12}$ colony forming unit (CFU) *Lactobacillus rhamnosus* CNCM I-4993 per gram (g) of composition according to embodiments of the invention. In further embodiments, the composition comprises $10^6$ to $10^{11}$ colony forming unit (CFU) *Lactobacillus rhamnosus* CNCM I-4993 per gram (g) of composition according to embodiments of the invention.

The bacterium as provided herein is suitable for use in edible compositions, accordingly in one embodiment the present invention provides a composition suitable for human consumption or ingestion, preferably by oral means. Accordingly the composition comprises or consists of comestible matter. It is particularly preferred that the compositions of embodiments of the invention are substantially free of pathogenic or toxicogenic matter. The composition according to embodiments of the invention may be a medicament or pharmaceutical composition. In a particularly preferred embodiment the composition according to the invention may be a non-therapeutic composition, preferably a nutraceutical composition, a nutritional composition and/or a food composition. It is particularly preferred that the food composition is a fermented food composition, preferably a fermented dairy composition. Further compositions according to embodiments of the invention also include food additives, food ingredients, nutritional formulas, baby foods, infant milk formulas and infant follow-on formulas.

The composition may comprise further additional strains of *Bifidobacterium* and/or lactic acid bacteria; typically 2, 3, 4 or more additional strains. Examples of *Bifidobacterium* that can be used include but are not limited to *Bifidobacterium animalis* (for example *Bifidobacterium animalis* subsp. *animalis* or *Bifidobacterium animalis* subsp. *lactis*); *Bifidobacterium longum*; *Bifidobacterium breve*; *Bifidobacterium bifidum*. Examples of lactic acid bacteria that can be used include but are not limited to *Lactobacilli* (for example *Lactobacillus acidophilus, Lactobacillus buchneri, Lactobacillus delbruckei*, in particular *L. delbrueckii* subsp. *bulgaricus* or *lactis, Lactobacillus casei, Lactobacillus plantarum, Lactobacillus reuteri, Lactobacillus johnsonii, Lactobacillus helveticus, Lactobacillus brevis, Lactobacillus rhamnosus*); *Streptococci* (for example *Streptococcus thermophilus*); *Lactococci* (for example *Lactococcus lactis*, typically *Lactococcus lactis* subsp. *lactis* or *Lactococcus lactis* subsp. *cremoris*). Preferably the composition further comprises *Lactobacillus* and/or *Streptococcus*. For the preparation of yogurt, the composition typically comprises *Lactobacillus bulgaricus* (also referred to as *Lactobacillus delbrueckii* subsp. *bulgaricus*) and *Streptococcus thermophilus*, optionally with additional microorganisms such as but not limited to probiotic species or other species that may provide desirable organoleptic or other qualities to the composition, e.g. further strains of *Lactococcus lactis*.

Accordingly in one embodiment the present invention provides a composition comprising *Lactobacillus rhamnosus* CNCM I-4993 and further comprising at least one strain of *Lactobacillus bulgaricus*, at least one strain of *Streptococcus thermophilus* and optionally one or more strains of *Lactococcus lactis* and/or *Bifidobacterium*.

Dairy Compositions.

In one embodiment the present invention provides a dairy composition, preferably a fermented dairy composition. The dairy composition of the invention comprises milk, preferably fermented milk. Preferably the composition comprises at least about 30% (w/w) milk, more preferably at least about 50% (w/w) milk and even more preferably at least about 70% (w/w) milk. In embodiments, the composition comprises at 30% to 100% (w/w) milk. In embodiments, the composition comprises 50% to 100% (w/w) milk. In embodiments, the composition comprises 70% to 100% (w/w) milk. Preferably said milk is vegetal and/or animal milk, more preferably soya, almond, oat, hemp, spelt, coconut, rice, goat, ewe, camel, mare or cow milk, and most preferably to cow milk. Preferably said milk(s) are heat-treated, typically pasteurized, to ensure sterility. Preferably said heat treatment is carried out prior to the preparation of the fermented dairy composition.

Preferably said milk comprises one or more of skimmed, partially-skimmed or non-skimmed milk. Preferably said milk or milks may be in liquid, powdered and/or concentrated form. In one embodiment said milk further comprises milk components preferably selected from the group consisting of cream, casein, caseinate (for example calcium or sodium caseinate), whey proteins notably in the form of a concentrate (WPC), milk proteins notably in the form of a concentrate (MPC), milk protein hydrolysates, and mixtures thereof. In one embodiment said mixture further comprises plant and/or fruit juices. In one embodiment said milk or milks may be enriched or fortified with further milk components or other nutrients such as but not limited to vitamins, minerals, trace elements or other micronutrients.

Preferably the dairy composition comprises above about 0.3 g per 100 g by weight free lactic acid, more preferably above about 0.7 g or 0.6 g per 100 g by weight free lactic acid. In embodiments, the composition comprises 0.3 g to 0.7 grams per 100 g by weight free lactic acid.

Preferably the dairy composition comprises a protein content at least equivalent to that of the milk or milks from which it is derived, preferably at least about 2.5%, more preferably at least about 3% or 3.5% (w/w). Preferably the composition has a pH equal to or lower than 5, preferably between about 3 and about 4.5 and more preferably between about 3.5 and about 4.5.

Preferably the dairy composition has a viscosity lower than 200 mPa·s, more preferably lower than 100 mPa·s and most preferably lower that 60 mPa·s, at 10° C., at a shear rate of 64 s$^{-1}$. In embodiments, the composition has a viscosity range of 1 to 200 mPa·s, 1 to 100 mPa·s, or 1 to 60 mPa·s, at 10° C., at a shear rate of 64 s$^{-1}$. In embodiments, the composition has a viscosity range of 10 to 200 mPa·s, 10 to 100 mPa·s, or 10 to 60 mPa·s, at 10° C., at a shear rate of 64 s$^{-1}$. In embodiments, the composition has a viscosity range of 30 to 200 mPa·s, 30 to 100 mPa·s, or 30 to 60 mPa·s, at 10° C., at a shear rate of 64 s$^{-1}$.

The fermented dairy composition according to embodiments of the invention is preferably a product selected from the group comprising yogurt, set yogurt, stirred yogurt, pourable yogurt, yogurt drink, frozen yogurt, kefir, buttermilk, quark, sour cream, fresh cheese and cheese. In one embodiment the composition according to embodiments of the invention is a drinkable composition, more preferably a fermented milk drink such as but not limited to a yogurt drink, kefir etc. In an alternative embodiment the composition according to embodiments of the invention is a composition that is spoonable, such as a set or stirred yogurt or equivalent thereof.

In one embodiment the fermented dairy composition is a strained fermented dairy composition. The strained fermented dairy composition preferably has the following contents (% by weight):
from 8.5% to 11.0% of milk protein
from 0.0% to 8.0% of fat, for example from 0.0% to 3.5% or from 3.5% to 8.0%
from 0.00% to 4.20% of lactose, for example from 2.80% to 4.20%

The pH of the strained fermented dairy composition can for example be of from 3.80 to 4.65.

Preferably the composition, according to embodiments of the invention, may be stored, transported and/or distributed at a temperature of from 1° C. to 10° C. for at least about 30 days, at least about 60 days or at least about 90 days from packaging and remain suitable for consumption.

In embodiments, the dairy compositions of the invention comprise at least $10^5$ cfu/g, more preferably at least $10^6$ cfu/g, such as at least $10^7$ cfu/g, e.g. at least $10^8$ cfu/g, such as at least $10^9$ cfu/g, e.g. at least $10^{10}$ cfu/g, such as at least $10^{11}$ cfu/g *Lactobacillus rhamnosus* CNCM I-4993 per gram of dairy composition. In embodiments, the compositions of the invention comprise $10^5$ to $10^{12}$ or $10^6$ to $10^{10}$ colony forming unit (CFU) *Lactobacillus rhamnosus* CNCM I-4993 per gram of composition.

Preferably, the composition is a packaged product that comprises at least $10^6$, more preferably at least $10^7$ and most preferably at least $10^8$ colony forming unit (CFU) *Lactobacillus rhamnosus* CNCM I-4993 per gram (g) of composition according to embodiments of the invention subsequent to storage, transport and/or distribution at a temperature of from 1° C. to 10° C. for at least about 30 days, at least about 60 days or at least about 90 days from packaging.

In embodiments, the composition is a packaged product that comprises $10^5$ to $10^{12}$ or $10^6$ to $10^{10}$ colony forming unit (CFU) *Lactobacillus rhamnosus* CNCM I-4993 per gram (g) of composition according to embodiments of the invention subsequent to storage, transport and/or distribution at a temperature of from 1° C. to 10° C. for at least about 30 days, at least about 60 days or at least about 90 days from packaging.

In embodiments, the dairy composition further comprises an intermediate preparation. Intermediate preparations are known to the one skilled in the art. They are typically used to modify the taste, mouthfeel and/or texture of a dairy composition, for example of a fermented dairy composition. They can used also to introduce some additives such as nutrients. They typically comprise sweetening agents, flavors, color modifiers, cereals and/or fruit. Intermediate fruit preparations are for example slurries or fruit preparations. Flavors include for example fruit flavors, vanilla flavors, caramel flavors, coffee flavors, chocolate flavors.

Fruit preparations typically comprise fruits, as used herein the term "fruit" refers to any fruit form, including for example full fruits, pieces, purees, concentrates, juices etc.

The intermediate preparation or slurry typically comprises a stabilizing agent, having at least one stabilizer. The stabilizing agent can comprise at least two stabilizers. Such stabilizers are known to the one skilled in the art. They typically help in avoiding phase separation of solids, for examples of fruits or fruits extracts and/or in avoiding syneresis. They typically provide some viscosity to the composition, for example a viscosity (Bostwick viscosity at 20° C.) of from 1 to 20 cm/min, preferably of from 4 to 12 cm/min.

The stabilizing system or the stabilizer can for example be a starch, a pectin, a guar, a xanthan, a carrageenan, a locust bean gum, or a mixture thereof. The amount of stabilizing system is typically of from 0.5 to 5% by weight.

The intermediate preparation can typically comprise organoleptic modifiers. Such ingredients are known by the one skilled in the art.

The organoleptic modifiers can be for example sweetening agents different from sugar, coloring agents, cereals and/or cereal extracts.

Examples of sweetening agents are ingredients referred to as High Intensity Sweeteners, such as sucralose, acesulfamK, aspartam, saccharine.

Examples of fruits include for example strawberry, peach, apricot, mango, apple, pear, raspberry, blueberry, blackberry, passion, cherry, and mixtures or associations thereof, such as peach-passion.

The fruits can be for example provided as:
frozen fruit cubes, for example 10 mm fruit cubes, for example Individual Quick Frozen fruit cubes, for example strawberry, peach, apricot, mango, apple, pear fruit cubes or mixtures thereof,
Aseptic fruit cubes, for example 10 mm fruit cubes, for example strawberry, peach, apricot, mango, apple or pear fruit cubes or mixtures thereof,
fruit purees, for example fruit purees concentrated from 2 to 5 times, preferably 3 times, for example aseptic fruit purees, for example strawberry, peach, apricot, mango, raspberry, blueberry or apple fruit purees or mixtures thereof,
single aseptic fruit purees, for example strawberry, raspberry, peach, apricot, blueberry or apple single aseptic fruit purees or mixture thereof,
frozen whole fruits, for example Individual Quick Frozen whole fruits, for example blueberry, raspberry or blackberry frozen whole fruits, or mixtures thereof,
mixtures thereof.

The ingredients and/or components of the intermediate preparation and the amounts thereof can be typically such that the composition has a brix degree of from 1 to 65 brix, for example from 1 to 10 brix, or from 10 to 15 brix, or from 15 to 20 brix, or from 20 to 25 brix, or from 25 to 30 brix, or from 30 to 35 brix, or from 35 to 40 brix, or from 40 to 45 brix, or from 45 to 50 brix, or from 50 to 55 brix, or from 55 to 60 brix, or from 55 to 60 brix, or from 60 to 65 brix.

A fruit preparation can for example comprise fruit in an amount of from 30% to 80% by weight, for example from 50 to 70% by weight.

The intermediate preparation can comprise water. It is mentioned that a part of the water can come from ingredients used to prepare the fruit preparation, for example from fruits or fruit extracts or from a phosphoric acid solution.

The fruit preparation can comprise pH modification agents such as citric acid. The fruit preparation can have a pH of from 2.5 to 5, preferably of from 2.8 to 4.2.

Typically a fruit preparation can be added in an amount of 5-35% by weight with reference to the total amount of composition. In embodiments the composition of the invention comprises up to about 30% (w/w) of said intermediate preparation, e.g. up to about 10%, 15%, 20%, 25% (w/w). In one embodiment, the composition according to embodiments of the invention comprise 1% to 30% (w/w) of said intermediate preparation. In alternative embodiments, the composition according to embodiments of the invention comprise 1% to 25% (w/w) of said intermediate preparation. In further alternative embodiments, the composition according to embodiments of the invention comprise 1% to 20% (w/w) of said intermediate preparation. In additional embodiments, the composition according to embodiments of the invention comprise 1% to 15% (w/w) of said intermediate preparation. In further additional embodiments, the composition according to embodiments of the invention comprise 1% to 10% (w/w) of said intermediate preparation.

Preferably the composition, according to embodiments of the invention is provided in a sealed or sealable container containing about 50 g, 60 g, 70 g, 75 g, 80 g, 85 g, 90 g, 95 g, 100 g, 105 g, 110 g, 115 g, 120 g, 125 g, 130 g, 135 g, 140 g, 145 g, 150 g, 200 g, 300 g, 320 g or 500 g or about 1 oz, 2 oz, 3 oz, 4 oz, 5 oz, 6 oz or 12 oz product by weight.

In embodiments, the composition, according to embodiments of the invention is provided in a sealed or sealable container containing about 50 g to 500 g, 60 g to 500 g, 70 g to 500 g, 75 g to 500 g, 80 g to 500 g, 85 g to 500 g, 90 g to 500 g, 95 g to 500 g, 100 g to 500 g, 105 g to 500 g, 110 g to 500 g, 115 g to 500 g, 120 g to 500 g, 125 g to 500 g, 130 g to 500 g, 135 g to 500 g, 140 g to 500 g, 145 g to 500 g, 150 g to 500 g, 200 g to 500 g, 300 g to 500 g, 320 g to 500 g or 500 g product by weight. In embodiments, the composition, according to embodiments of the invention is provided in a sealed or sealable container containing about 1 oz to 12 oz, 2 oz to 12 oz, 3 oz to 12 oz, 4 oz to 12 oz, 5 oz to 12 oz, 6 oz to 12 oz or 12 oz product by weight.

Inoculum Compositions

The bacterium as described herein is useful as starter culture in the preparation of food compositions, such as fermented dairy products. Accordingly, in one embodiment the present invention provides an inoculum comprising *Lactobacillus rhamnosus* CNCM I-4993 that is suitable for the preparation of fermented dairy products. The inoculum of the invention is suitable for the direct inoculation *Lactobacillus rhamnosus* CNCM I-4993 into a composition comprising milk to provide fermented dairy products of the invention, typically without the need for a culture step prior to the said direct inoculation.

Typically the inoculum further comprises excipient or carriers, the selection of which is within the scope of the skilled person but may include buffers or culture media. The inoculum may optionally comprise further components such as cryoprotectants, preservatives and/or additives including nutrients such as yeast extracts, cysteine, sugars and vitamins.

Typically the inoculum is for use in the preparation of fermented dairy products, according in one embodiment the inoculum of the invention may be provided to the dairy composition in quantities of up to about 500 mg/l.

Typically the inoculum is fresh, frozen, dried or lyophilized. The inoculum may be in liquid, dry, spray-dried or solid form. It is particularly preferred that the inoculum is in liquid form. The inoculum may be defrosted and/or dispersed in liquid (e.g. water) prior to inoculation into a composition comprising milk.

In embodiments, the inoculum comprises at least $10^9$ cfu, e.g. at least $10^{10}$ cfu, such as at least $10^{11}$ cfu *Lactobacillus rhamnosus* CNCM I-4993 per gram of inoculum composition. In embodiments, the inoculum comprises $10^9$ to $10^{12}$ colony forming unit (CFU), or more preferably $10^{10}$ to $10^{12}$ colony forming unit (CFU) *Lactobacillus rhamnosus* CNCM I-4993 per gram of inoculum.

Typically the inoculum comprising *Lactobacillus rhamnosus* CNCM I-4993 is substantially pure.

In a further embodiment the present invention provides a mixture or kit of parts of the inoculum of the invention together with inoculum of *Bifidobacterium* and/or lactic acid bacteria.

Examples of *Bifidobacterium* that can be used include but are not limited to *Bifidobacterium animalis* (for example *Bifidobacterium animalis* subsp. *animalis* or *Bifidobacterium animalis* subsp. *lactis*); *Bifidobacterium longum*; *Bifidobacterium breve*; *Bifidobacterium bifidum*. Examples of lactic acid bacteria that can be used include but are not limited to *Lactobacilli* (for example *Lactobacillus acidophilus, Lactobacillus buchneri, Lactobacillus delbrueckii*, in particular *L. delbrueckii* subsp. *bulgaricus* or *lactis, Lactobacillus casei, Lactobacillus plantarum, Lactobacillus reuteri, Lactobacillus johnsonii, Lactobacillus helveticus, Lactobacillus brevis, Lactobacillus rhamnosus*); *Streptococci* (for example *Streptococcus thermophilus*); *Lactococci* (for example *Lactococcus lactis*, typically *Lactococcus lactis* subsp. *lactis* or *Lactococcus lactis* subsp. *cremoris*). Preferably the inoculum mixture further comprises *Lactobacillus* and/or *Streptococcus*. For the preparation of yogurt, the inoculum mixture typically comprises *Lactobacillus bulgaricus* (also referred to as *Lactobacillus delbruckei* subsp. *bulgaricus*) and *Streptococcus thermophilus*, optionally with additional microorganisms such as but not limited to probiotic species or other species that may provide desirable organoleptic or other qualities to the composition, e.g. *Lactococcus lactis*.

Accordingly in one embodiment the present invention provides an inoculum mixture comprising a *Lactobacillus rhamnosus* CNCM I-4993 inoculum and further comprising at least one inoculum of *Lactobacillus bulgaricus*, at least one inoculum of *Streptococcus thermophilus* and optionally one or more additional inoculum of *Lactococcus lactis* and/or *Bifidobacterium*.

Methods for the Preparation of Fermented Dairy Products

The bacterium as provided herein is suitable for use in the preparation of fermented dairy products. Accordingly in a third aspect the present invention also relates to the intended use of *Lactobacillus rhamnosus* CNCM I-4993 for the preparation of a food composition.

The present invention provides a process for the preparation of a fermented dairy product comprising inoculating a milk-based composition with *L. rhamnosus* CNCM I-4993 and fermenting.

Accordingly in one embodiment the present invention provides a process comprising the following steps:
i) providing a mixture comprising:
 a) milk
 b) *Lactobacillus rhamnosus* CNCM I-4993
ii) fermentation of said mixture to provide a fermented dairy product.

Preferably fermented dairy products are prepared using milk that has been subjected to heat treatment at least equivalent to pasteurization. Preferably said heat treatment is carried out prior to the preparation of the composition.

Typically, milk is pasteurized by means of the following successive steps:

1) standardization of fatty substances of the raw material so as to obtain a standardized substance,
2) enrichment with dried matter of the standardized substance obtained in the preceding stage, so as to obtain an enriched substance,
3) preheating of the enriched substance obtained in the preceding stage, so as to obtain a starting substance,
4) pasteurization and holding of the starting substance obtained in the preceding stage, so as to obtain a pasteurized and held substance,
5) an optional stage of homogenization of the pasteurized and held substance obtained in the preceding stage, so as to obtain a pasteurized, held and optionally homogenized substance,
6) initial cooling of the pasteurized, held and optionally homogenized substance obtained in the preceding stage, so as to obtain a pasteurized starting substance that has been held, optionally homogenized, and cooled down.

As used herein "standardization of fatty substances" is taken to mean a stage of bringing the quantity of fats present in the starting substance to a pre-determined level. Enrichment with dried matter involves the addition of proteins and fatty substance in order to modify curd firmness.

As used herein "holding" is taken to mean a rapid heating and maintenance of temperature of the milk and makes it possible to destroy the vegetative microbial flora, including pathogenic forms. Its typical duration is from 4 to 10 minutes, in particular from 5 to 8 minutes, and in particular approximately 6 minutes.

As used herein "homogenization" is taken to mean the dispersion of the fatty substances in the milk-type substance into small fat globules. The homogenization is carried out for example at a pressure of 100 to 280 bars, in particular 100 to 250 bars, in particular 100 to 200 bars, in particular approximately 200 bars. This homogenization stage is purely optional. It is in particular absent from the production process of products with 0% fatty substances.

Typically a fermented dairy product is prepared by culture of milks at a suitable temperature with suitable microorganisms to provide a reduction in pH, preferably to a pH equal to or lower than 5, preferably between about 3 and 4.7; more preferably between about 3.5 and about 4.7. The pH can be adjusted by controlling the fermentation by the microorganism and stopping it when appropriate, for example by cooling.

According to a further embodiment of the process for the preparation of a fermented dairy product as defined above, the mixture comprising milk and *Lactobacillus rhamnosus* CNCM I-4993 further comprises at least one, two, three or more strains of *Bifidobacterium* and/or lactic acid bacteria. The selection of suitable *Bifidobacterium* strains is within the scope of the skilled person and is typically a probiotic lactic acid bacteria. Examples of *Bifidobacterium* that can be used include but are not limited to *Bifidobacterium animalis* (for example *Bifidobacterium animalis* subsp. *animalis* or *Bifidobacterium animalis* subsp. *lactis*); *Bifidobacterium longum*; *Bifidobacterium breve*; *Bifidobacterium bifidum*.

The selection of suitable lactic acid bacteria strains is within the scope of the skilled person and is typically a thermophillic lactic acid bacteria. Examples of lactic acid bacteria that can be used include but are not limited to *Lactobacilli* (for example *Lactobacillus acidophilus, Lactobacillus buchneri, Lactobacillus delbruckei*, in particular *L. delbrueckii* subsp. *bulgaricus* or *lactis, Lactobacillus casei, Lactobacillus plantarum, Lactobacillus reuteri, Lactobacillus johnsonii, Lactobacillus helveticus, Lactobacillus brevis, Lactobacillus rhamnosus*); *Streptococci* (for example *Strep-* tococcus thermophilus); Lactococci (for example *Lactococcus lactis*, typically *Lactococcus lactis* subsp. *lactis* or *Lactococcus lactis* subsp. *cremoris*). Typically a mixture or association of a plurality of species of lactic acid bacteria may be used, typically a mixture or association of *Lactobacillus* and *Streptococcus*. For the preparation of yogurt this typically includes *Lactobacillus bulgaricus* (also referred to as *Lactobacillus delbrueckii* subsp. *bulgaricus*) and *Lactobacillus rhamnosus*, optionally with additional microorganisms such as but not limited to probiotic species or other species that may provide desirable organoleptic or other qualities to the composition, e.g. *Lactococcus lactis*.

Accordingly in one embodiment the mixture further comprises at least one strain of *Lactobacillus bulgaricus*, at least one strain of *Streptococcus thermophilus* and optionally one or more strains of *Lactococcus lactis* and/or *Bifidobacterium*.

Suitable temperatures for milk fermentation are typically about 36° C. to about 44° C. and the temperature is maintained for an incubation time sufficient to provide the desired reduction in pH. For the preparation of a fermented dairy product the temperature at the start of fermentation is typically about 36° C. to about 43° C., in particular about 37° C. to about 40° C., the temperature at the end of fermentation is typically about 37° C. to about 44° C., in particular about 38° C. to about 41° C. The fermentation time is typically about 6 to about 11 hours.

Subsequent to the fermentation the fermented milk is cooled. Optionally a stage of intermediate cooling of the fermented milk may be performed to provide a pre-cooled fermented milk having a temperature of between about 22° C. and about 4° C. Typically the intermediate cooling time is about 1 hour to about 4 hours, in particular about 1 hour 30 minutes to about 2 hours. The pre-cooled fermented milk is typically stored for up to 40 hours or less.

Preferably a stage of final cooling of the fermented milk is performed such that the temperature at the start of the final cooling is less than about 22° C. and the temperature at the end of the final cooling is about 4° C. to about 10° C. The cooled product may then be stored, transported and/or distributed at a temperature from about 1° C. to about 10° C. for at least about 30 days, at least about 60 days or at least about 90 days.

According to a further embodiment, the process for the preparation of a fermented dairy product as defined above optionally comprises a stage of stirring at a pressure of at least 20 bars, or performing a dynamic smoothing, to obtain a composition having the desired viscosity, typically a viscosity of up to 20 mPa·s. Stirring or dynamic smoothing operations provide some shear to composition that typically allow a viscosity drop. Such operations are known by the one skilled in the art, and can be operated with conventional appropriate equipment. This stage is typically performed at cold temperature, for example at a temperature of form 1° C. to 20° C. Without intending to be bound to any theory, it is believed that applying some shear at cold temperature, typically by stirring at high pressure or by performing a dynamic smoothing, can lead to a fluid gel formation within the composition, that provides improved stability even at a low viscosity of up to 20 mPa·s.

Alternatively, according to a further embodiment, the process for the preparation of a fermented dairy product as defined above optionally comprises a stage of acid whey removal to provide a "strained fermented dairy composition". In this step an acid whey composition is separated from the curd resulting from the protein coagulation due to acidification during fermentation. Thus one obtains:

a fermented dairy product, typically comprising the proteins coagulum, referred to as a strained fermented dairy composition, and an acid whey by-product Such separation steps are known by the one skilled in art, for example in processes of making "greek yogurts". The separation can for example be carried out by reverse osmosis, ultrafiltration, or centrifugal separation. The separation step can be performed for example at a temperature of from 30° C. to 45° C.

According to a further embodiment, the process for the preparation of a fermented dairy product as defined above optionally comprises a stage of addition of an intermediate preparation as described above prior or subsequent to fermentation, said intermediate preparation typically comprising a preparation of fruits and/or cereals and/or additives such as flavorings and/or colourings.

The invention will be further illustrated by the following non-limiting Figures and Example.

EXAMPLES

Example 1: Strain Selection

A total of 65 strains of *Lactobacillus* and *Bifidobacterium* were screened for production of acetoin & diacetyl. The strains included 37 *Bifidobacterium*, 3 *Streptococcus salivarius* subspecies *thermophilus* and 25 *Lactobacillus* (4 *L. delbrueckii*, 1 *L. helveticus*, 1 *L. amylovorus*, 3 *L. jonhsonii*, 6 *L. paracasei*, 8 *L. rhamnosus* and 2 *L. plantarum*).

Reconstituted milk was prepared by mixing 110 g skimmed milk powder (Arla) per litre permuted water and pasteurized at 95° C. for 45 minutes. Each strain was grown in milk for 16 hours at 37° C. and acetoin & diacetyl production was analyzed by static head space gas chromatography using a Autosystem XL GC fitted with a flame ionization detector (Perkin Elmer, Waltham, US). Concentration of acetoin and diacetyl (ppm) in samples was determined using response factors coming from standards.

Figure 1:
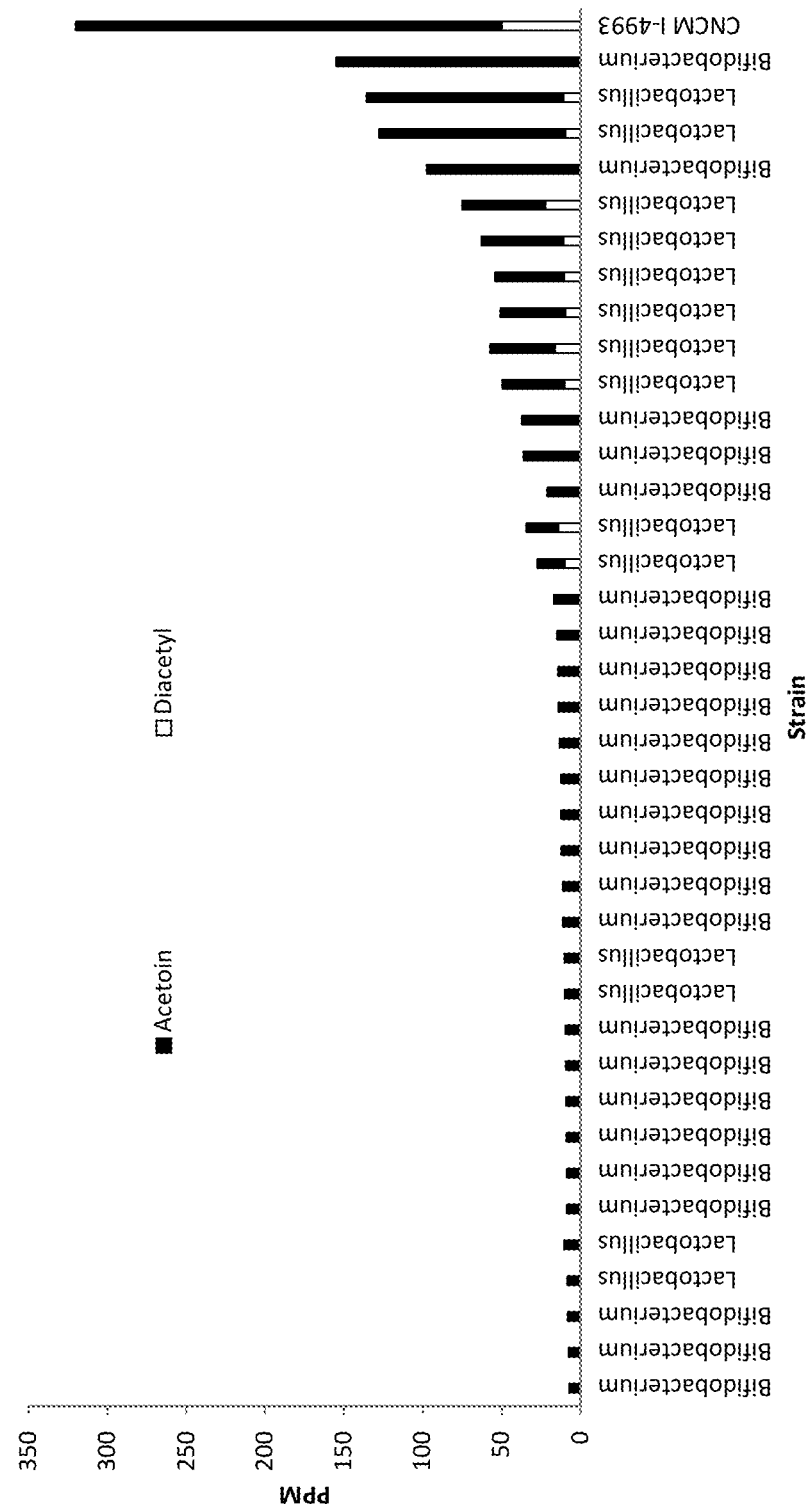
FIG. 1 shows the levels of acetoin and diacetyl in parts per million (PPM) produced by 20 bacterial strains tested according to Example 1.

Of the 65 tested strains only 20 strains were able to produce at least 6 ppm of acetoin. Results are provided for these 20 strains in FIG. 1. As can be seen the strain of the invention was the best producer of both acetoin & diacetyl. The combined amount of acetoin & diacetyl produced was more than twice the amount of the next best strain.

Example 2: Milk Fermentation

Reconstituted milk was prepared by mixing 112 g skimmed milk powder (Arla) per litre permuted water and pasteurized at 99° C. for 30 minutes. Bacteria strains were provided in the form of frozen pellets, L. rhamnosus CNCM I-4993 was supplied by Danone. Strains were inoculated in reconstituted milk after defrosting. Fermentation was carried out at 37° C. and monitored using a pH probe. L. rhamnosus CNCM I-4993 was tested in 2 batches, each batch consisting of 3 individual tests at various inoculation rates.

Results

| | Lag phase (minutes) | pH at max. acidification velocity | Time to pH 4.5 (minutes) |
|---|---|---|---|
| Batch 1 Test 1 Innoculation 0.01% volume | 445 | 5.61 | 1948 |
| Batch 1Test 2 Innoculation 0.02% volume | 353 | 5.59 | 1652 |
| Batch 1Test 3 Innoculation 0.01% volume | 443 | 5.54 | 1852 |
| Batch 2 Test 1 Innoculation 0.01% volume | 416 | 5.90 | 988 |
| Batch 2Test 2 Innoculation 0.02% volume | 328 | 5.80 | 940 |
| Batch 2Test 3 Innoculation 0.01% volume | 428 | 5.46 | 1632 |

Figure 5:
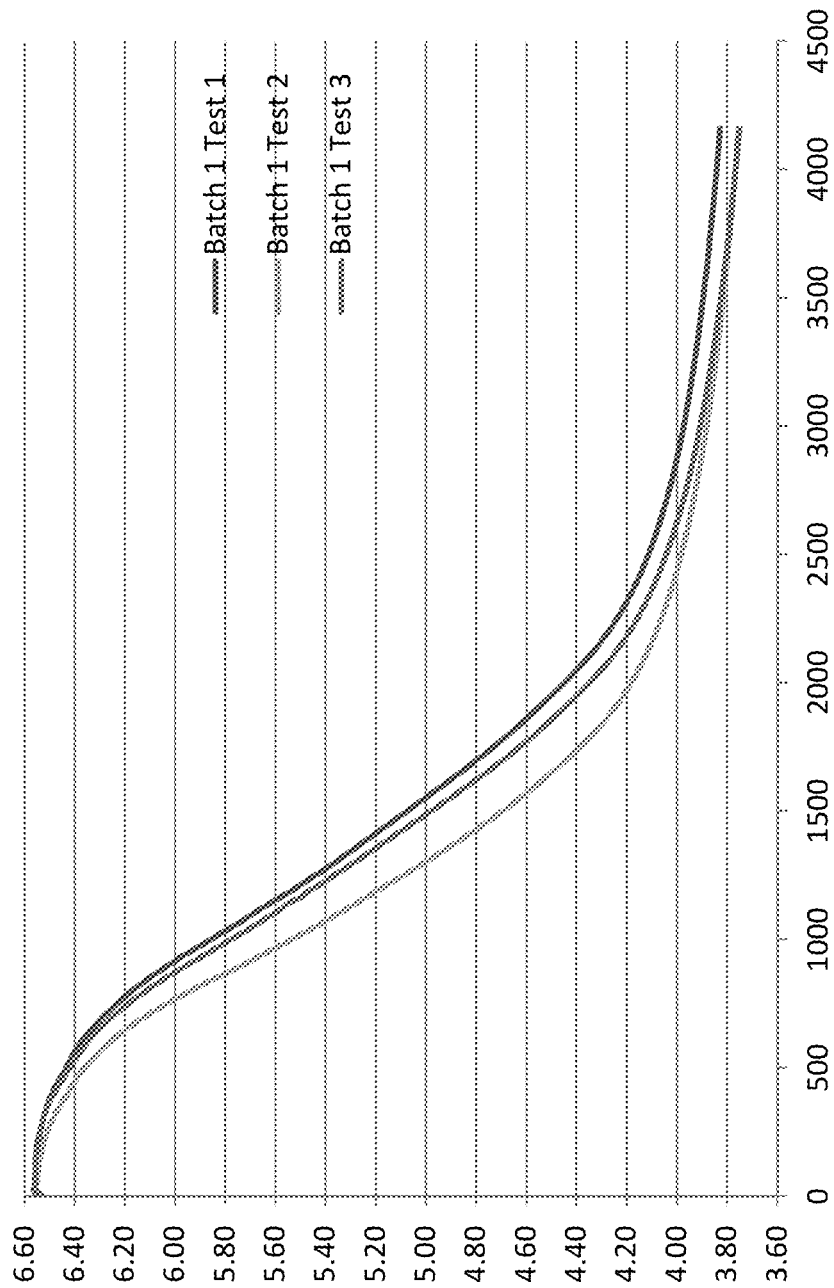
FIG. 5 shows the milk acidification kinetics of Batch 1 carried out according to Example 2. Time in minutes is provided on the x-axis, pH is represented on the y-axis.

Acidification curves of Batch 1 are provided in FIG. 5.

Example 3: Fermented Milk Product Preparation & Sensory Evaluation

Figure 4:
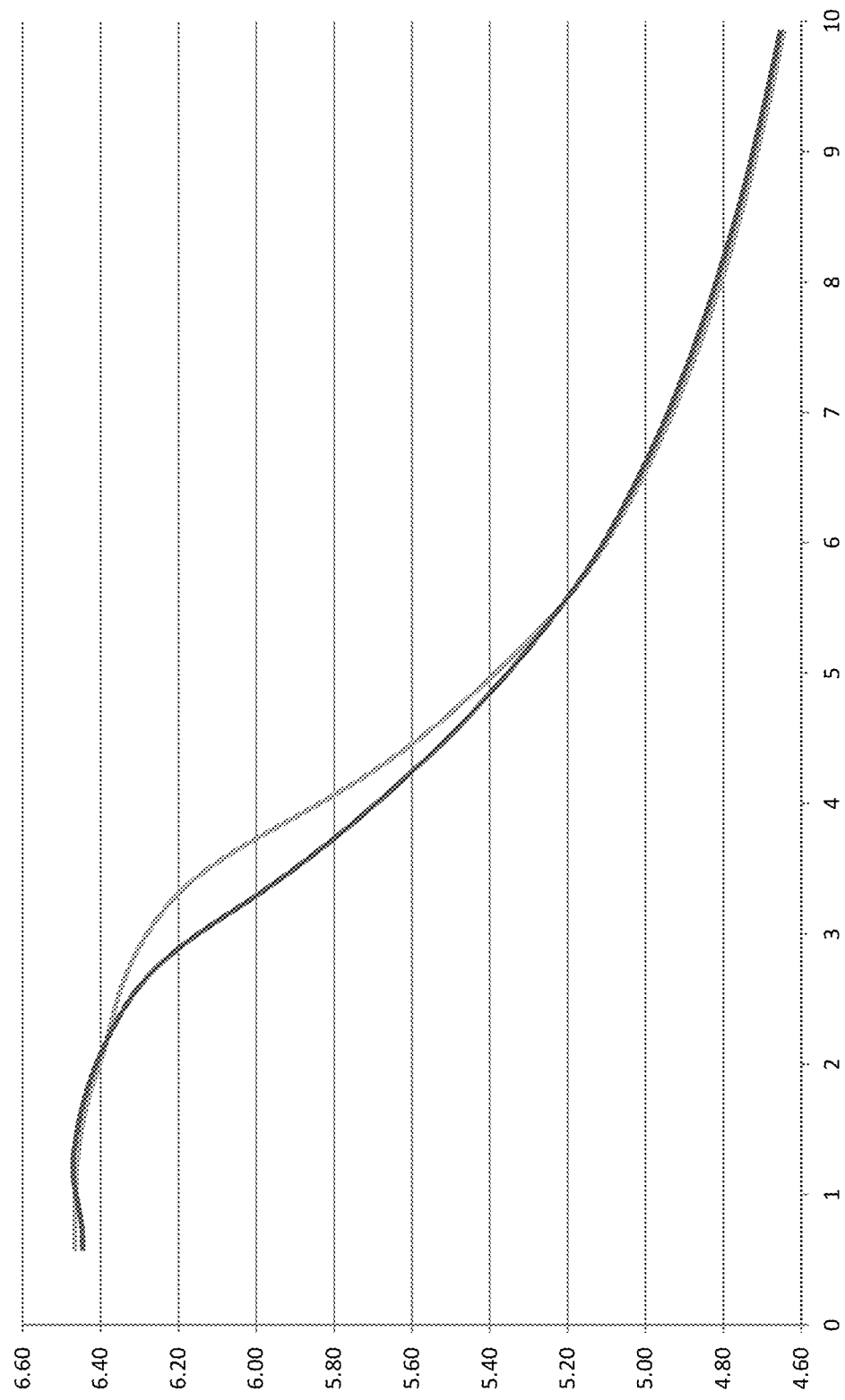
FIG. 4 shows the milk acidification kinetics of control and test products prepared according to Example 3. Time in hours is provided on the x-axis, pH is represented on the y-axis. The dark grey plot represents the test product, the light grey plot represents the test product.

A fermented milk product was prepared by fermentation of a pasteurized milk base (6.64% skim milk powder; 93.06% milk; 0.3% whey protein concentrate) with a standard yogurt starter culture (L. delbrueckii, S. thermophilus & yeast extract) as control product. The control product ferment was supplemented with L. rhamnosus CNCM I-4993 to prepare a test product by fermentation of said milk base. Fermentation kinetics are provided in FIG. 4, as can be seen the test product had a higher initial rate of acidification.

Figure 2:
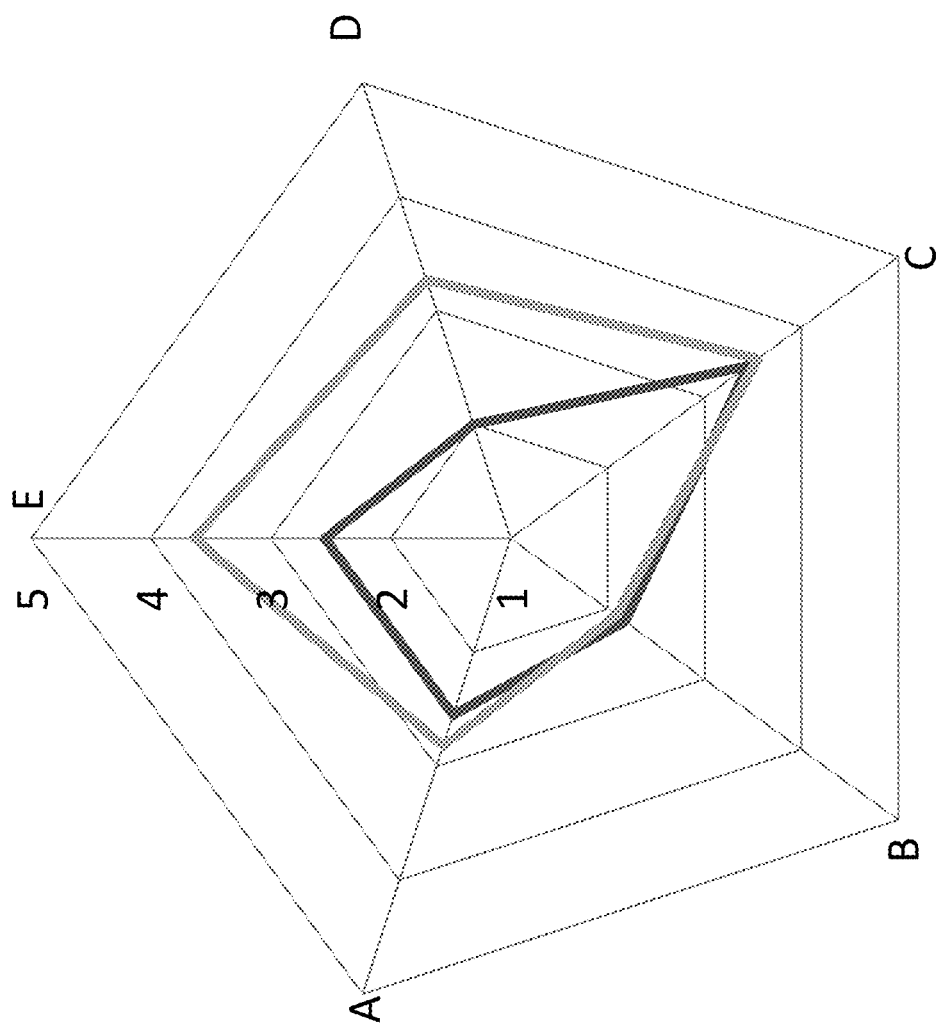
FIG. 2 shows the global sensory profile of test and control products evaluated by consumer according to Example 3. Each sensory characteristic is evaluated on a scale of 1-5 and the plot shows the average of the 11 testers: A=dairy notes, B=sweetness, C=acidity, D=thickness in mouth, E=thickness in spoon. The dark grey plot represents the control product, the light grey plot represents the test product.
Figure 3:
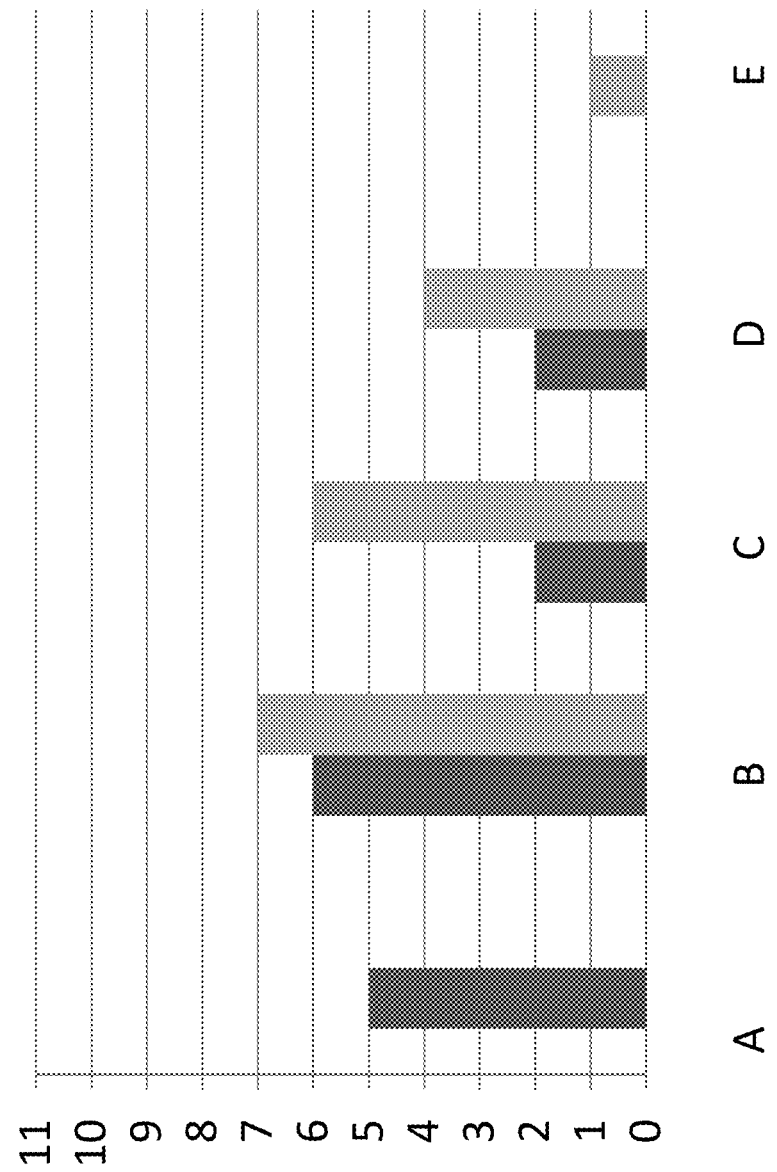
FIG. 3 shows the dairy notes flavour profile of test and control products evaluated by consumer according to Example 3. X-axis shows the frequency of identification of a specified dairy note characteristic in the 11 testers. Dairy notes are provided in the Y-axis: A=milky, B=yogurt acidity, C=creamy, D=cheesy, E=buttery. Dark grey bars represent the control product, light grey bars represent the test product.

Sensory evaluation was carried out by 11 testers who evaluated the dairy notes of the flavour profile and a global sensory profile of the control and test products. The testers assessed the organoleptic characteristics dairy notes (A), sweetness (B), acidity (C), thickness in mouth (D), thickness in spoon (E) on a scale of 1 to 5. Average values for all characteristics were used to generate average value scores for each characteristics, these results are provided in FIG. 2. FIG. 3 shows the frequency of identification of the characteristics by the panel. These results demonstrate that the test product was thicker in the spoon and mouth. The addition of the strain of the invention also changed the flavour profile of the fermented dairy product, providing a product that was clearly more creamy, cheesy and buttery but that was also perceived as less milky while providing a good level of acidity that is considered standard in fermented milk products such as yogurt.

The invention claimed is:

1. A dairy composition comprising milk and *Lactobacillus rhamnosus* strain deposited at CNCM under reference number I-4993.

2. The dairy composition according to claim 1, comprising at least $10^5$ CFU/g of the *Lactobacillus rhamnosus* strain.

3. The dairy composition according to claim 2, wherein said dairy composition is an inoculum.

4. The dairy composition according to claim 3, wherein said dairy composition is fresh, frozen, dried or lyophilized.

5. The dairy composition according to claim 1, wherein said dairy composition is a yogurt.

6. The dairy composition according to claim 1, wherein said dairy composition is a fermented composition.

7. The dairy composition according to claim 1, further comprising at least one, two, three or more strains of *Bifidobacterium* or lactic acid bacteria.

8. The dairy composition according to claim 7, wherein said dairy composition is fresh, frozen, dried or lyophilized.

9. The dairy composition according to claim 7, wherein said dairy composition comprises at least two strains of lactic acid bacteria, wherein said strains of lactic acid bacteria comprise at least one strain of *Lactobacillus bulgaricus* and at least one strain of *Streptococcus thermophilus*.

10. The dairy composition according to claim 9, further comprising one or more strains selected from the group consisting of *Lactococcus lactic* and/or *Bifidobacterium*.

11. The dairy composition of claim 1, wherein the milk is vegetal milk.

12. The dairy composition of claim 11, wherein the vegetal milk is soya, almond, oat, hemp, spelt, coconut, or rice milk.

13. The dairy composition of claim 1, wherein the milk is animal milk.

14. The dairy composition of claim 13, wherein the animal milk is goat, ewe, camel, mare or cow milk.

15. A method for the preparation of a fermented dairy product comprising
fermenting a mixture comprising:
a) milk; and
b) *L. rhamnosus* CNCM 1-4993
to provide a fermented dairy product.

16. The method according to claim 15, wherein the mixture comprises at least one, two, three or more strains of *Bifidobacterium* or lactic acid bacteria.

17. The method according to claim 16, wherein the mixture comprises at least two strains of lactic acid bacteria, wherein said strains of *lactic* acid bacteria comprise at least one strain of *Lactobacillus bulgaricus* and at least one strain of *Streptococcus thermophilus*.

18. A fermented food product comprising *Lactobacillus rhamnosus* strain deposited at CNCM under reference number I-4993.

* * * * *

UNITED STATES PATENT AND TRADEMARK OFFICE
CERTIFICATE OF CORRECTION

Page 1 of 1

PATENT NO. : 11,166,473 B2
APPLICATION NO. : 16/158165
DATED : November 9, 2021
INVENTOR(S) : Peggy Garault et al.

It is certified that error appears in the above-identified patent and that said Letters Patent is hereby corrected as shown below:

On the Title Page

Column 1, Please delete Item (30) Foreign Application Priority Data in its entirety.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*